United States Patent [19]

Mynatt

[11] 4,376,826
[45] * Mar. 15, 1983

[54] CONTINUOUS PRODUCTION OF BACTERIA FOR LEACHING OF METALLIC ORE

[76] Inventor: Roy L. Mynatt, 15362 DaCosta, Detroit, Mich. 48223

[*] Notice: The portion of the term of this patent subsequent to Mar. 16, 1999, has been disclaimed.

[21] Appl. No.: 160,285

[22] Filed: Jun. 17, 1980

[51] Int. Cl.$^3$ .............. C12N 1/20; C10G 32/00; C12M 1/14

[52] U.S. Cl. ......................... 435/253; 435/281; 435/282; 435/310; 435/804; 435/813

[58] Field of Search ............... 435/241, 253, 281, 282, 435/310, 262, 174, 176, 804, 813, 285, 287

[56] References Cited

U.S. PATENT DOCUMENTS

| | | | |
|---|---|---|---|
| 2,829,964 | 4/1958 | Zimmerley et al. | 435/262 X |
| 3,193,460 | 7/1965 | Krabbe et al. | 435/253 |
| 3,305,353 | 2/1967 | Duncan et al. | 435/282 X |
| 3,925,165 | 12/1975 | Müller | 435/310 X |
| 4,025,394 | 5/1977 | Young | 435/804 X |
| 4,153,510 | 5/1979 | Messing et al. | 435/176 |
| 4,320,198 | 3/1982 | Mynatt | 435/287 X |

*Primary Examiner*—David M. Naff
*Attorney, Agent, or Firm*—James M. Deimen

[57] ABSTRACT

Continuous production of bacteria for leaching metallic ore is carried out by inoculating the bacteria on a pitted plate, supplying a nutrient substrate to the bacteria to promote growth of the bacteria, periodically harvesting bacteria from the plate and conveying the harvested bacteria by sluice to a leaching site. Harvesting is preferably carried out by passing a blade over the plate to shear off bacteria above the surface of the plate leaving behind bacteria within the pits of the plate for continued bacteria growth.

6 Claims, 3 Drawing Figures

FIGURE I

CONTINUOUS PRODUCTION OF BACTERIA FOR LEACHING OF METALLIC ORE

BACKGROUND OF THE INVENTION

The field of invention pertains to the production of sessile bacteria for use in the leaching of metallic ores. The utility of bacteria, particularly the iron bacteria, to leach ore from spent sources is discussed at length in the following two papers:
CONFERENCE, BACTERIAL LEACHING, Ed. W. Schwartz, Braunschweig, 1977.
METALLURGICAL APPLICATIONS OF BACTERIAL LEACHING AND RELATED MICROBIOLOGICAL PHENOMENA, Eds., Murr, Torma, Bruerly, Academic Press, 1978.
The culturing of bacteria suitable for use in leaching of ore can be continuous as described in Murr, et al. Thus far however this continuous culturing has utilized only a single phase vortex method. More abundant growth of sessile bacteria is possible using the continuous culturing technique provided by U.S. Pat. No. 4,153,510. This patent provides for the continuous culturing of sessile bacteria on a pitted glass plate.

SUMMARY OF THE INVENTION

The invention comprises an apparatus and process for the growth and harvest of bacteria suitable for the leaching of metal ore. The bacteria grown on a pitted glass plate is mechanically harvested and transferred to ore leaching sites. A suitable micro-organism such as Leptothrix is grown on a pitted glass plate by supplying a suitable flowing nutrient substrate. With abundant pellicle growth the nutrient flow is temporarily halted and a blade passed over the plate harvesting the pellicle growth and depositing the harvest products onto a sluice conveyor. Upon retraction of the blade the nutrient substrate flow is restored until the harvest cycle is repeated again. The sluice conveyor conducts the products to the ore leaching site.

The disclosed process and apparatus thus produces and harvests bacteria suitable for the leaching of metal ore.

DESCRIPTION OF THE PREFERRED EMBODIMENTS

Figure 1:
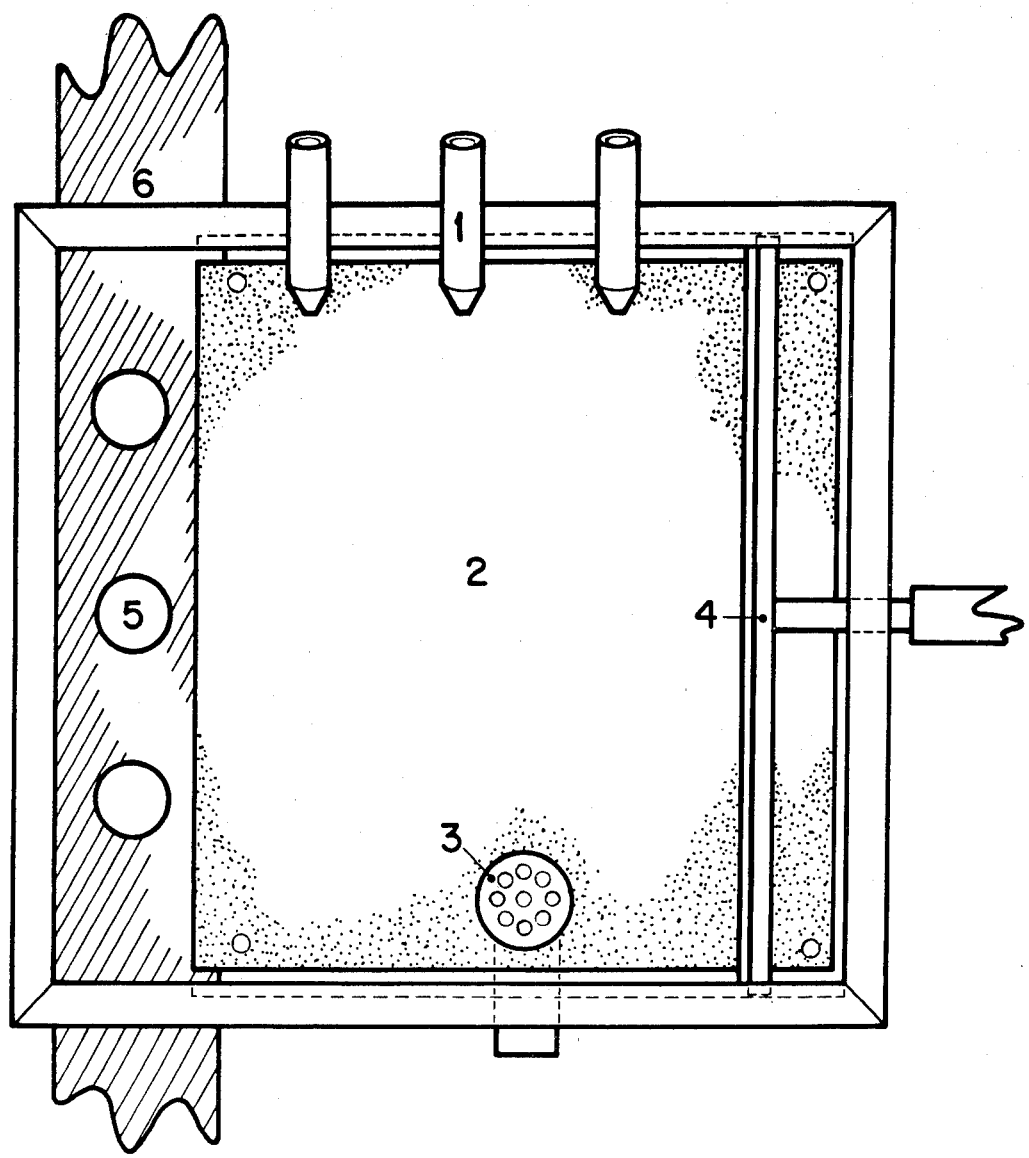
FIG. 1 is a top view of the continuous cultivation apparatus.
Figure 2:
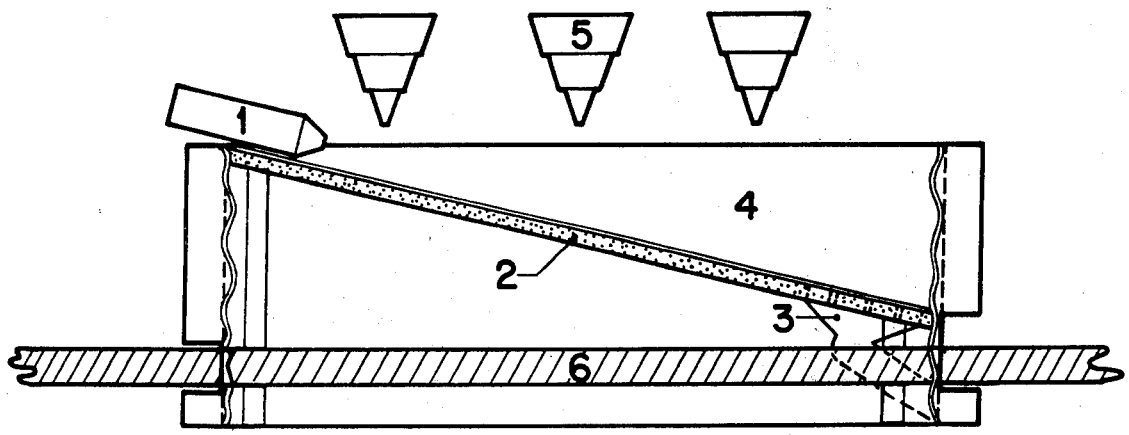
FIG. 2 is a cutaway front view of the cultivation apparatus.
Figure 3:
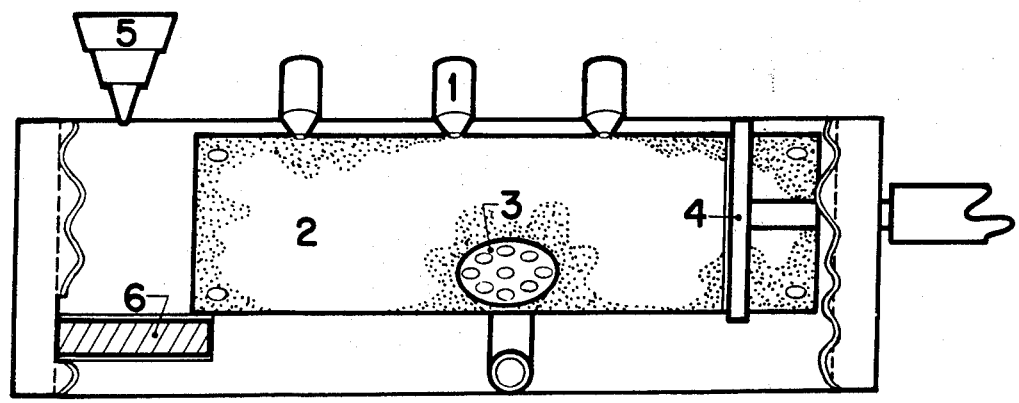
FIG. 3 is a cutaway side view of the cultivation apparatus.

As shown in FIGS. 1, 2, and 3, the apparatus includes a pitted glass plate 2 extending downwardly from a plurality of nozzles 1. The glass plate 2 is innoculated with a suitable bacteria as disclosed below. At the lower end of the plate 2 is a drain 3. A suitable nutrient is injected through the nozzles 1 and flows down the plate 2 and into the drain 3. The excess nutrient entering the drain 3 may be mixed with fresh nutrient and recycled through the nozzles 1.

A harvesting blade 4 is shown in a position near full retraction. The blade 4 may be extended across the plate 2 periodically by manual means or hydraulic or other suitable means to harvest the bacterial growth extending upwardly from the plate 2. The substrate flow is halted temporarily during the harvesting cycle.

As the blade 4 fully extends beyond the plate 2 and over the sluice 6, paper stock washers 5 inundate the blade 4 to wash the harvested products onto the sluice. The growth rate of the micro-organism determines the frequency of harvest. Effectively continuous production can be accomplished by a plurality of the apparatus units at various states of growth.

An example of a suitable micro-organism is the iron bacteria, Leptothrix. This organism grows in dense colonies with low nutrient requirements, good resistance to temperature variations and has good tolerance of a high rate of nutrient substrate flow over the plate 2. It thus resists contamination by other cultures without sophisticated sterilization techniques.

A suitable nutrient for continuous cultivation of Leptothrix, in the apparatus disclosed above would comprise:

(1) A nutrient composed of:
Bacto-peptone: 1 g/liter water
Bacto-dextrose: 1 g/liter water
Magnesium sulfate: 1.2 g/liter water
Calcium chloride: 0.05 g/liter water
Ferric chloride: 0.001 g/liter water
Bacto-agar: 12.5 g/liter water
(2) Final pH=7.0
(3) Nutrient temperature 25° C. or room temperature
(4) Flow rate=1.49 ft./sec.

Alternatively its known Leptothrix occurs in naturally occuring colonies growing on brewery, pulp mill, cannery and other wastes which may be utilized economically in connection with its growth in this apparatus.

I claim:
1. A process for the production of bacteria suitable for the leaching of metallic ore comprising the steps of:
    innoculating a pitted plate with a bacteria adapted to the leaching of metallic ore,
    supplying a nutrient substrate to the bacteria sufficient to promote abundant growth of the bacteria desired,
    periodically harvesting the bacterial growth extending above the pitted plate by passing a blade over the plate to shear off and collect the bacterial growth above the surface of the plate leaving behind the bacteria within the pits of the pitted plate, and,
    conveying the products by sluice to the leaching site.
2. The process of claim 1 wherein the nutrient flows over the plate.
3. The process of claims 1 or 2 wherein the bacteria is Leptothrix.
4. The process of claims 1 or 2 wherein the bacteria is Thiobacillus ferrooxidans.
5. The process of claim 1 wherein the nutrient substrate includes at least one component selected from the group consisting of brewery, pulp mill or cannery wastes.
6. The process of claim 1 wherein the flow of nutrient substrate is temporarily halted during harvesting movement of the blade.

* * * * *